United States Patent [19]

Pollack

[11] 4,285,341
[45] * Aug. 25, 1981

[54] EXTRACORPOREAL CANNULA APPARATUS WITH RETRACTABLE INTRALUMENAL BALLOON AND METHOD FOR USING SAME

[76] Inventor: Charles N. Pollack, 12311 Windsor Dr., Carmel, Ind. 46032

[*] Notice: The portion of the term of this patent subsequent to Feb. 20, 1996, has been disclaimed.

[21] Appl. No.: 78,607

[22] Filed: Sep. 24, 1979

Related U.S. Application Data

[63] Continuation-in-part of Ser. No. 962,909, Nov. 22, 1978, which is a continuation-in-part of Ser. No. 796,362, May 12, 1977, Pat. No. 4,140,119.

[51] Int. Cl.³ .................. A61M 1/03; A61M 25/00
[52] U.S. Cl. .................. 128/214 R; 128/348; 128/349 B
[58] Field of Search ................ 128/348–351, 128/214 R, 214.4, 240–241, 246, 344, 325

[56] References Cited

U.S. PATENT DOCUMENTS

| 2,919,697 | 1/1960 | Kim | 128/349 B |
|---|---|---|---|
| 3,331,371 | 7/1967 | Rocchi et al. | 128/349 B |
| 3,392,722 | 7/1968 | Jorgensen | 128/350 R |
| 3,395,710 | 8/1968 | Stratton et al. | 128/350 R |
| 3,995,617 | 12/1976 | Watkins et al. | 128/348 |
| 4,024,873 | 5/1977 | Antoshkiw et al. | 128/349 B |
| 4,140,119 | 2/1979 | Pollack | 128/348 |
| 4,186,745 | 2/1980 | Lewis et al. | 128/349 R |
| 4,202,346 | 5/1980 | Granier | 128/349 B |

FOREIGN PATENT DOCUMENTS 485204 12/1975 U.S.S.R. .................. 128/349 B

Primary Examiner—Bradley Garris
Attorney, Agent, or Firm—Woodard, Weikart, Emhardt & Naughton

[57] ABSTRACT

An improved extracorporeal cannula apparatus suitable for use in a cardiac cannulation including a first elongated and flexible tube having an open proximal end and a distal end with at least one hole therein. At least one inflatable balloon is positionable within the lumen of the first tube adjacent the distal holes and is inflatable to occlude the cannula lumen and prevent the entrapment of air near the distal end. In the preferred apparatus, the balloon also extends to a point between the most distal portion and the most proximal portion of the holes thereby only partially obstructing the holes and permitting liquid to freely flow through the unobstructed portion of the distal end. The inflatable balloon is positionable by means of a second flexible tube threaded through the cannula lumen and a side-mounted tube attached near the proximal end of the cannula. When cannulation is begun, the first balloon is deflated and withdrawn into this side arm to prevent any possible interference with blood flow through the cannula. A method is further provided for inserting this improved cannula into the circulatory system of a person during a cardiac cannulation.

24 Claims, 11 Drawing Figures

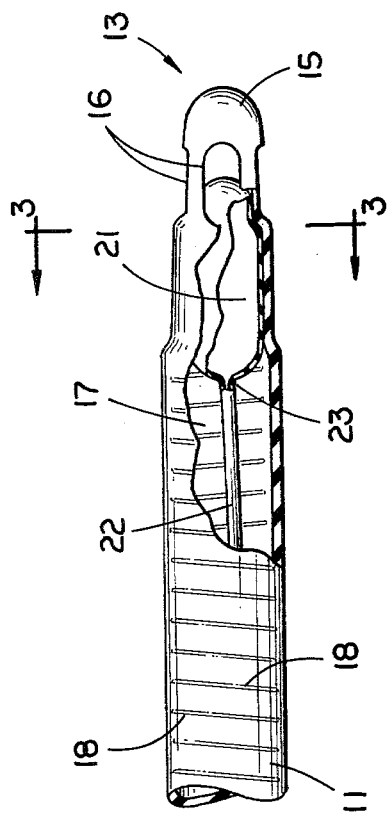
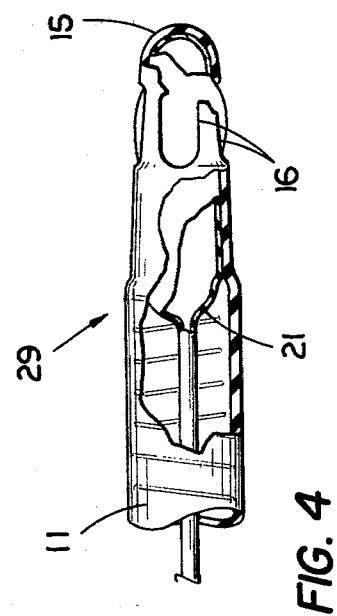
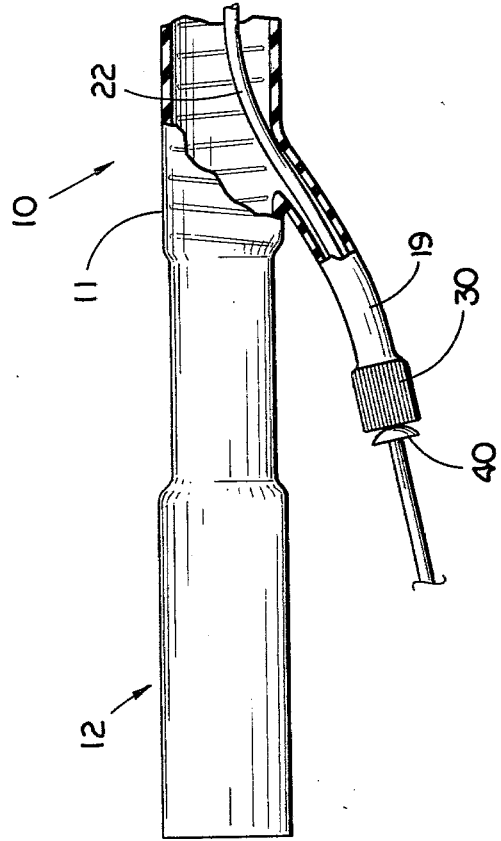
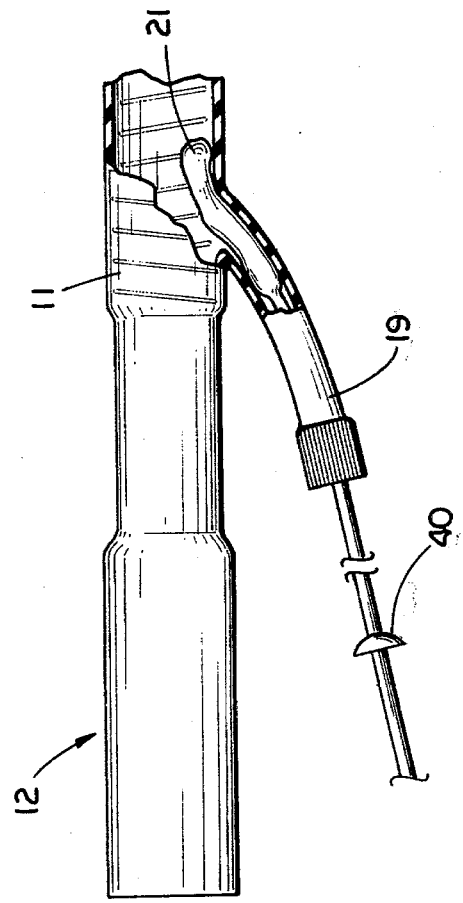

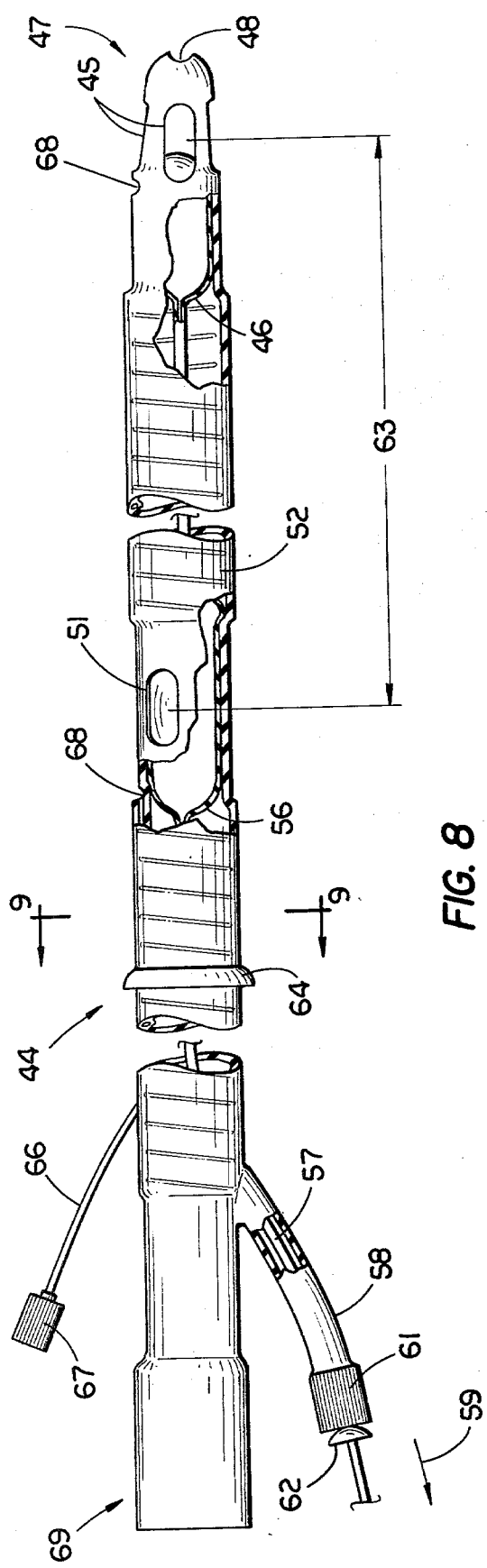
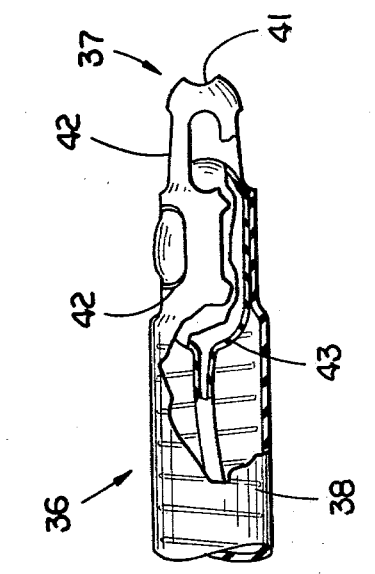
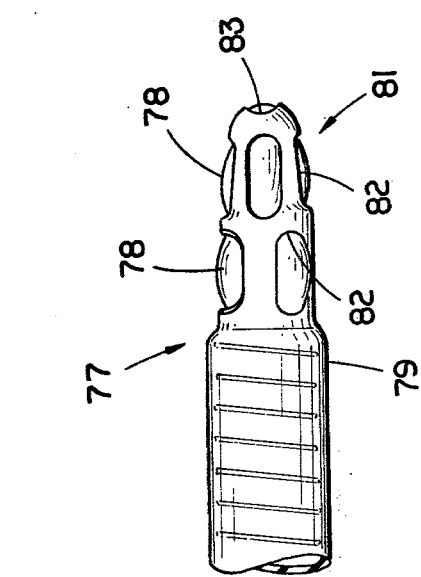
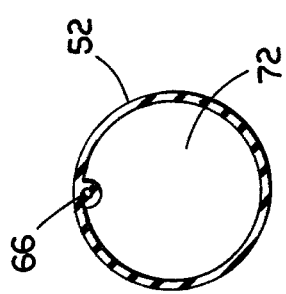

EXTRACORPOREAL CANNULA APPARATUS WITH RETRACTABLE INTRALUMENAL BALLOON AND METHOD FOR USING SAME

BACKGROUND OF THE INVENTION

This application is a continuation-in-part application of my previously filed U.S. patent application, Ser. No. 962,909, filed Nov. 22, 1978 and entitled "Balloon-Tipped Extracorporeal Cannula Apparatus and Method for Insertion of Same." U.S. Ser. No. 962,909 is in turn a continuation-in-part of my parent application, Ser. No. 796,362 filed May 12, 1977 of the same name, which has since issued as U.S. Pat. No. 4,140,119 on Feb. 20, 1979.

This invention relates to methods and apparatus used in cannulation techniques, and particularly, to an improved cannula apparatus and method for its insertion suitable for use in a cardiac cannulation.

A cannula, or catheter as it may be called, is generally recognized as an elongated and flexible tube that is inserted into a person's body in order to withdraw or inject various fluids. The prior art is replete with such cannulas and catheters, as well as with methods for their insertion and use.

The general use of inflatable balloons with such cannulas and catheters is also known in the art. In one instance, commonly referred to as a "bag" catheter, an externally attached balloon or "bag" is used to hold the catheter in place after insertion in order to allow prolonged or periodic withdrawal or injection of fluids into the body. A common use for such "bag" catheters, as disclosed in Rocchi et al., U.S. Pat. No. 3,331,371, is to insert the catheter by way of the urethra into a person's bladder in order to withdraw waste fluid from the bladder over a period of time. Another example of an externally attached inflatable balloon or collar used to stabilize the position of the cannula following insertion is found in Shinnick et al., U.S. Pat. No. 3,680,544, which discloses a transthoracic cannula-type device useful in cardiopulmonary resuscitation.

In other instances, inflatable balloons have been positioned inside the luminal cavity in the cannula or catheter in order to achieve a desired result. In Kim, U.S. Pat. No. 2,919,697, such an intraluminal inflatable balloon was used for the same purpose as described above, i.e., for anchoring the standard catheter drainage tube in the body after insertion. The above Rocchi reference, on the other hand, uses the intraluminal balloon or ball to completely cover the fluid holes in the catheter and thereby control the flow of fluid therethrough. Similar to the lumenal blockage disclosed in Stratton et al., U.S. Pat. No. 3,395,710, however, the blockage in Rocchi does not prevent air from being entrapped in the distal tip of the cannula upon insertion. Intralumenal balloons are also used in the blood flow arrester and surgical valve devices in the Russian Pat., Kanshin et al., No. 465204, and in Jorgensen, U.S. Pat. No. 3,392,722.

A rapidly-growing area of cannula technology concerns the technique of cardiac cannulation and the use of artificial heart-lung machines as a means to facilitate intricate and prolonged operations on the cardiac, pulmonary and circulatory systems. During such operations, cannulas which are connected to the artificial heart-lung machine means are first properly inserted through prepared incisions into the arterial and venous systems adjacent the heart, and even into the intracardiac chambers as well. Once properly positioned and in operation, the blood of the person is withdrawn or siphoned through the venous cannulas and pumped through the arterial cannulas back into the ciculatory system by the artificial heart-lung machine means. The heart and lungs of the person are thereby effectively bypassed, allowing the surgeon to operate on the heart and adjacent areas.

A major problem encountered in all such cardiac cannulation techniques involves the introduction of air into the circulatory system during the insertion and positioning of the various venous, arterial and intracardial cannulas. In this regard, the avoidance of any such introduction is extremely important because of the danger of stroke or other adverse effects air can have on the circulatory system.

The present state of the art provides two possible methods for avoiding any such introduction of air during cardiac cannulation. One method involves first inserting the distal end of the cannula into the circulatory system while the tubing connecting the cannula to the heart-lung machine means is then vented by manipulating a drain line near the proximal end of the cannula thereby permitting the cannula to fill with the patient's blood. This method, however, does not prevent the possible introduction of air into the blood stream during initial insertion of the distal end of the cannula. In addition, it requires the extra steps of manipulating both the venting line and the external clamp, and cannot prevent the probable entrapment of air in the tube between this venting line and the clamp itself.

A second method of cannula insertion practiced in the art involves first holding the cannula upright and filling it either with a serum or with blood through the plurality of holes near its distal tip. Then, the surgeon rapidly inserts the distal end of the cannula into the prepared incision in the circulatory system in order to avoid excessive spillage of the fluid, if at all possible. This method has its shortcomings both because of the mess created by the spilling fluid and because as the fluid empties, air is again allowed into the cannula and may be later introduced into the circulatory system.

In applicant's now-issued U.S. Pat. No. 4,140,119 identified above, applicant discloses a new cannula apparatus and method for its use that mark a significant advance in the art, particularly with regard to cardiac cannulation. The dangers of entrapped air during insertion and of the mess caused by fluid spillage and the extra steps now practiced are eliminated. In addition, the positioning of applicant's balloon within the cannula lumen permits the free flow of blood across and through the unobstructed portion of the holes in the distal end of the cannula after its insertion into the circulatory system and prior to deflation of the balloon.

In applicant's earlier continuation-in-part application, U.S. Ser. No. 962,909, filed Nov. 22, 1978, applicant discloses and claims several modifications of his base cannula invention. These improvements expand upon applicant's earlier invention providing for specific uses and modifications important in various surgical techniques such as cardiac cannulation.

SUMMARY OF THE INVENTION

One aspect of this invention comprises a further improvement of applicant's cannula apparatus disclosed and claimed in its earlier filed applications. This improvement comprises at least one inflatable balloon movable within the cannula lumen. Means are provided for positioning the balloon adjacent the holes in the distal end to once again occlude the lumen and prevent the entrapment of air near the distal end when the balloon is inflated. Means are also provided for retracting or removing the balloon from the cannula lumen after it is deflated. In this way, the deflated balloon does not remain within the lumen during use and there is therefore no possibility of it interfering with blood flow during the cannulation procedure. Once cannulation is completed, however, the balloon can be repositioned and reinflated or the cannula can be simply clamped to assist with its removal and prevent any excess blood spillage or loss.

Several modes are available for practicing applicant's most recent improvement. For example, positioning of the balloon near the distal end can be such as to prevent air entrapment while permitting liquid to wash or flow freely across and through the remaining unobstructed portion of the distal end and holes. The number of holes near the cannula end and the positioning of a hole in the distal tip itself are also available as modifications. Furthermore, a second plurality of holes can be spaced apart proximally along the cannula member from these distal holes. A second inflatable balloon, either separate or communicating with the first balloon, is then similarly positioned with respect to these more proximal holes to prevent the entrapment or introduction of air into the circulatory system of a person while permitting drainage of blood from two adjacent but separate areas during cannulation, e.g., the left ventricle and left atrium areas. A still further modification is the provision of an infusion passageway or tube in the main cannula body to permit infusion of a variety of solutions into the heart or adjacent vessels during a cannulation procedure.

A second aspect of this invention is a method for using the improved cannula apparatus described above in a cardiac cannulation procedure. This method is improved and distinct over both the prior art and applicant's prior inventions for many of the same reasons attributed to applicant's improved apparatus.

Related objects and advantages of the present invention will be apparent from the following description.

BRIEF DESCRIPTION OF THE DRAWINGS

FIG. 1 is a fragmented side elevation of the improved balloon-tipped extracorporeal cannula comprising a preferred embodiment of the present invention with portions broken away.

FIG. 2 is a partial side elevation of the cannula in FIG., 1 with a portion broken away to reveal the balloon deflated and retracted within the side member.

FIG. 3 is a cross-sectional view of the cannula in FIG. 1 taken along line 3—3.

FIG. 4 is a partial side elevation of a modified cannula apparatus in accordance with one embodiment of this invention with a portion broken away to reveal the first balloon when inflated.

FIG. 7 is a partial side elevation of a modified cannula apparatus in accordance with one embodiment of this invention, with a portion broken away to reveal the first balloon when inflated.

FIG. 8 is a fragmented side elevation of a third modified cannula apparatus in accordance with one embodiment of this invention, with portions broken away to reveal the inflated and properly positioned first and second intralumenal balloons.

FIG. 9 is a cross-sectional view of the cannula in FIG. 8 taken along line 9—9.

FIG. 11 is a partial side elevation of a fourth modified cannula apparatus in accordance with one embodiment of this invention.

DESCRIPTION OF THE PREFERRED EMBODIMENTS

Figure 5:
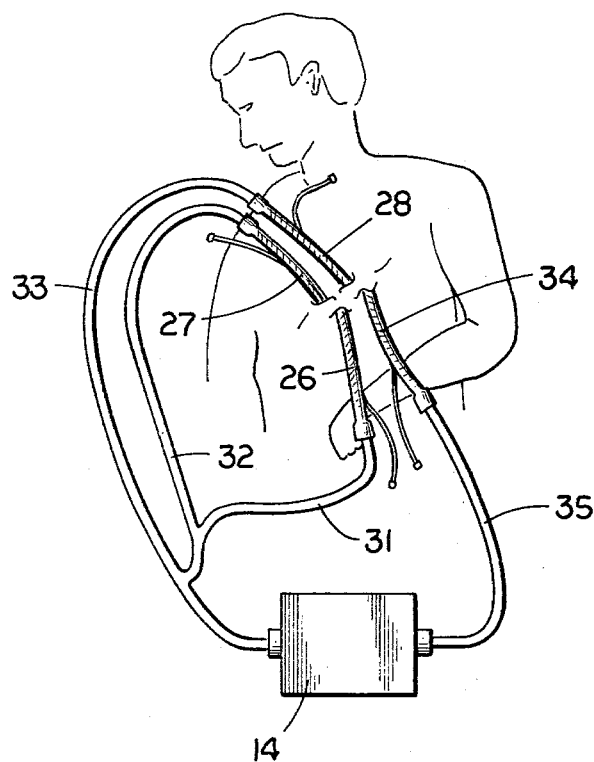
FIG. 5 is a reduced representation of four balloon-tipped extracorporeal cannulas of the present invention, as shown in FIG. 1, in use during a cardiac cannulation.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

Referring now to FIG. 1, the improved balloon-tipped cannula 10 comprising a preferred embodiment of the present invention is therein depicted. Cannula 10 includes a first elongated and flexible tube 11 which has both a proximal end 12 and a distal end 13. The proximal end of cannula 10 is open to allow the cannula to be attached to various secondary tubing which then connects the cannula to the desired equipment, such as the heart-lung machine means 14 in FIG. 5. Distal end 13, on the other hand, has a closed and thickened distal tip 15 and includes a plurality of holes 16 near this distal tip which allow fluid to flow between the lumen 17 of cannula 10 and the circulatory system of the person.

Tube 11 of the preferred embodiment is made of a flexible material, such as rubber or polyvinyl. It may also include a spiraling wire 18 which is molded into the cannula wall 24. This wire 18 reinforces the central portion of cannula 10 thereby facilitating easy handling and preventing any possibility of the cannula collapsing or being pinched shut and thus closing off the flow of blood to or from the patient. Other ways of reinforcing the tubular body of a cannula are known in the art and will adapt equally well to the present invention. In addition, no reinforcement may be needed if the tube material is sufficiently strong.

The dimensions of tube 11 may vary greatly according to the person's age and size, the number of cannulas used in the cannulation technique and the specific manufacturer of the cannulas used. The external cross-sectional diameter of the tube 11 may thus vary from about 1 cm. to about 2 cm. at its widest point, tube 11 of the preferred embodiment being about 1.5 cm. in diameter.

A first inflatable balloon 21 is positioned within the lumen 17 of tube 11 adjacent to and proximal of the holes 16. A second elongated and flexible tube 22 connects with inflatable balloon 21 at point 23 as shown in FIG. 1. Tube 22 then connects the balloon 21 to a supply of fluid (not shown) which is used to inflate and deflate the balloon during use of the cannula 10. Air may be used as a satisfactory inflating substance, however, it is desirable to use a liquid such as a saline solution because of the possible danger of a leak developing in the balloon which then could introduce air into the circulatory system of the person.

Many fluid supplies and means of inflating and deflating balloon 21 may be used in conjunction with the invention. In the preferred embodiment, however, tube 22 extends through a third flexible tubular member 19 attached to the cannula wall 24 at a point removed from the distal end 13. Tube 22 further threads through a sealed adapter 30 on this side arm 19 and connects at a point not shown to a female attachment or adapter which receives a nipple tip syringe (also not shown). This syringe is used to inject or withdraw fluid through tube 22 thereby inflating and deflating the balloon.

Manipulation of tube 22 further provides the means for properly positioning and retracting first balloon 21 within the cannula lumen 17 during a cannulation procedure. This mobility of the inflatable balloon is an improvement over applicant's previous cannula invention having the balloon mounted on the inside wall 24 of tube 11 at a point adjacent to and proximal of the holes 16. When inflated, this stationary balloon performs equally well as applicant's present invention in occluding the lumen of the cannula and preventing the entrapment of any air near the distal end while also permitting the free flow of liquid through the unobstructed portion of this end. When deflated, however, the stationary balloon collapses against the inside wall 24 of the cannula providing some, although minor, obstruction to blood flow during removal or injection through the cannula body.

Applicant has now discovered that even the minimal obstruction provided by this stationary collapsed balloon may interfere with blood flow sufficient to constitute a potential problem in some cannulation procedures. In an effort to eliminate even this minimal interference, applicant discovered the present modification described and claimed herein. In this regard, applicant's previous applications, U.S. Ser. No. 962,909 and U.S. Ser. No. 796,362, which is now U.S. Pat. No. 4,140,119, are hereby incorporated herein by reference as to all relevant and material disclosure contained therein.

Figure 6:
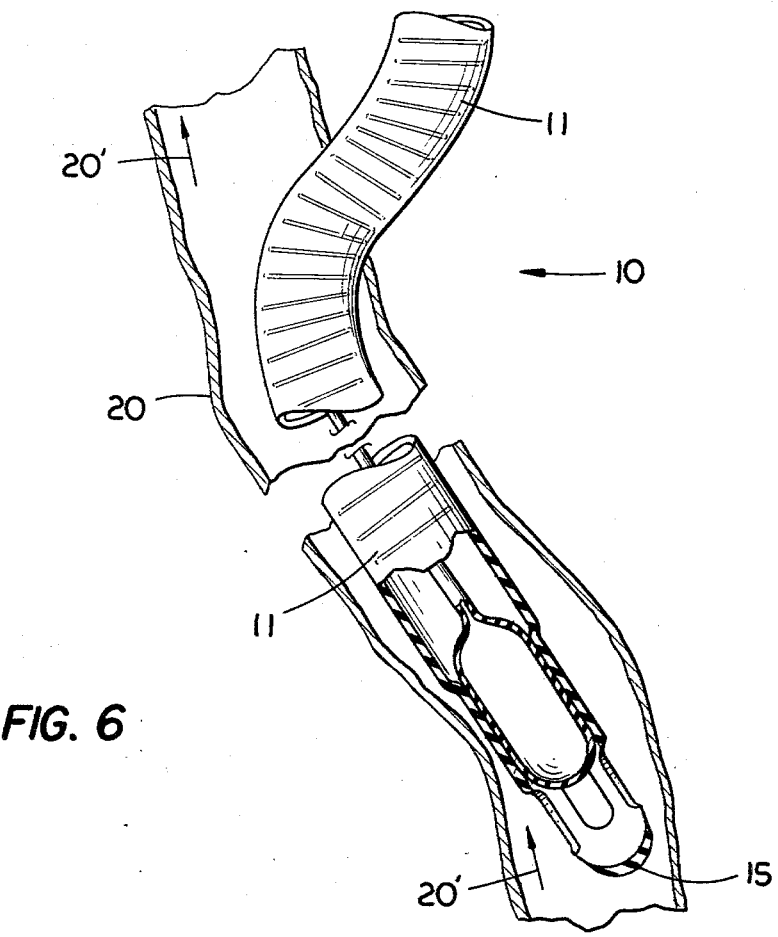
FIG. 6 is a part-sectional view of the distal end of the cannula in FIG. 1 positioned in the inferior vena cava adjacent a person's heart during a cardiac cannulation.

Specifically, prior to insertion of the cannula during a surgical application, balloon 21 is positioned as shown in FIG. 1 by manually threading inflation tube 22 through the passageway in side arm or tube 19 and its sealed adapter 20. When inflated, as shown in FIGS. 1, 3, and 6, balloon 21 completely occludes the lumen 17 of preferred cannula 10. The most distal portion 25 of the balloon 21 also extends to a point between the most distal portion and most proximal portion of the holes 16 near the distal end of tube 11. FIG. 3 depicts a cross-sectional view of cannula 10 in FIG. 1 taken at the most proximal portion of the holes 16. As it reveals, the inflated balloon completely occludes the cannula lumen at that point thereby preventing the flow of any fluid through the cannula. More importantly, by occluding the lumen 17 right up to the holes 16, the inflated balloon also prevents the entrapment of any air in the tube 11 proximal of holes 16 and thereby avoids the possible introduction of any such entrapped air into the circulatory system upon insertion of the cannula.

As previously discussed, an additional feature of the balloon-tipped extracorporeal cannula of the preferred embodiment is that the inflated balloon only partially obstructs the holes 16 near the distal end 13 of the cannula. Therefore, no air can be trapped in the closed distal tip during insertion, and the person's blood may be able to wash or flow across and through the unobstructed portion of the distal end of tube 11 if it becomes wedged or stuck in a vessel or chamber after its insertion and prior to deflation of the balloon 21. This minimizes the possibility of interference with normal blood flow prior to initiating the artificial heart-lung action and thus provides less chance of vessel obstruction impairing the flow of blood through the circulatory system. FIG. 6 depicts a venous cannula 10 of the present invention positioned in an inferior vena cava 20 during a cardiac cannulation and prior to deflation of the balloon. The blood is flowing in the direction of arrow 20'.

Once cannula 10 is properly positioned within the person's body, balloon 21 is deflated so that the cannulation procedure can begin. However, rather than lying against the inside wall of the tube, the collapsed balloon and inflation tube are both totally retracted, or withdrawn, from the lumen back into the side passageway in tube 19, as shown in FIG. 2. This removal is accomplished by once again manipulating tube 22 this time in the direction of arrow 59 as shown in FIG. 8. Once fully retracted within the side arm, there is no possibility of the collapsed balloon or tube obstructing or interfering with the free flow of blood through lumen 17 during the cannulation procedure.

When surgery is completed and further cannulation not required, balloon 21 is again properly positioned as shown in FIG. 1 and inflated to stop the flow of blood in the cannula by simply threading tube 22 through adapter 30. In this regard, although several means are known and available to assist the surgeon in properly positioning the balloon either prior to or after cannulation, this is accomplished in preferred cannula 10 by use of a marker 40 attached to the outside of tube 22 as shown in FIG. 1.

A second embodiment of the present invention comprises a method of inserting the preferred cannula 10 into the circulatory system of a person during a cardiac cannulation procedure. The first two steps in this method involve filling the lumen 17 of the cannula with a fluid and then properly positioning and inflating balloon 21 as shown in FIG. 1. For this purpose, the order of these steps is unimportant and the filling step may be accomplished through either the proximal or distal end of the cannula using either blood or any compatible electrolyte such as a saline solution. In the preferred method, the balloon is first properly positioned and inflated prior to filling the lumen through the proximal end 12.

The distal end of the filled and occluded cannula is then inserted into the circulatory system of the person through a prepared incision. The lumen is unoccluded and cannulation is begun by next deflating the balloon and retracting the balloon and tube 22 within side arm 19 thereby permitting fluid to flow freely and without interference between the cannula and the circulatory system of the person.

FIG. 5 depicts the preferred method and balloon-tipped extracorporeal cannula of the present invention in use during a cardiac cannulation. Venous cannulas 26 and 27, constructed according to the present invention, are first positioned in the superior and inferior vena cava, respectively. An intracardial cannula 28 is also positioned inside the left ventricle of the heart in order to decompress the heart and keep the volume of blood in it minimal thereby preventing any possibility of the heart distending during the operation. These cannulas are in turn connected through tubing 31, 32 and 33, respectively, to the input side of a heart-lung machine means 14. An arterial cannula return line 34 is then positioned in the aorta or femoral artery in order to recirculate the blood from the heart-lung machine means 14 through tubing 35 and back into the circulatory system of the person.

In practice, both the number and location of the cannulas used in a cardiac cannulation technique can vary according to a variety of factors, such as the specific type of operation involved. In the preferred embodiments, four cannulas are used in order to assure proper and complete cannulation. The cannulas are first properly inserted into the circulatory system according to the above-described method. Then, when all four are properly positioned, the balloons are deflated and removed from the cannula lumen and the siphoning and recirculating action through the heart-lung machine means 14 is begun. At this time, the surgeon can operate on the person's heart, lungs or adjacent vessels while the machine 14 artificially maintains the heart and lung functions. When the operation is completed, the cannulas are occluded either by again properly positioning and inflating the intraluminal balloons or by simply clamping the cannulas thus allowing the person's heart and lungs to resume their normal functions.

Turning now to FIG. 7, a partial view of a modified cannula 36 in accordance with the present invention is therein depicted. Specifically, cannula 36 is substantially similar to cannula 10 of the preferred embodiment, with but a few modifications. First, the distal end 37 of flexible tubular member 38 includes a hole 41 in the distal tip thereof. Second, cannula 36 includes more holes 42 near the distal end 37 of the cannula.

First balloon 43 is constructed similar to preferred balloon 21 in that upon proper positioning and inflating, it extends to a point between the most distal portion and the most proximal portion of the holes 42 nearest the distal tip. By so doing, it prevents the entrapment of any air in the distal end of the cannula during insertion into the circulatory system of a person. First balloon 43, when inflated, also completely occludes the lumen of first member 38 and blocks, or occludes, all of the more proximal holes 42 near distal end 37. In this way, no air can be trapped in the distal end 37 and no liquid spillage can occur during insertion of the cannula.

In addition, once the cannula is inserted and first balloon 43 is deflated and retracted into its corresponding side arm passageway (not shown in FIG. 7), the additional holes permit the blood to flow more freely through the distal end of the cannula during operation of the heart-lung machine means (not shown). Still another advantage of modified cannula 36 is that after its insertion and prior to deflation of first balloon 43, hole 41 in the distal tip permits the freer flow of the person's blood across and through the unobstructed portion of the distal end of first member 38. This further minimizes the possibility of interference with normal blood flow prior to intiating the artificial heart-lung action and provides less chance of vessel obstruction or tissue buildup in the cannula tip which might impair, or block, the flow of blood through the circulatory system.

FIG. 8 depicts a further modification of a cannula apparatus in accordance with the present embodiments. Specifically, cannula 44 includes a plurality of holes 45 and a first inflatable balloon 46 similar in all respects to the holes 16 and balloon 21 of preferred cannula 10. The distal end 47 of cannula 44 also includes a hole 48 in the distal tip thereof to further enhance the free wash, or flow, of liquid through the unobstructed portion of distal end 47 when inserted in the circulatory system.

Figure 10:
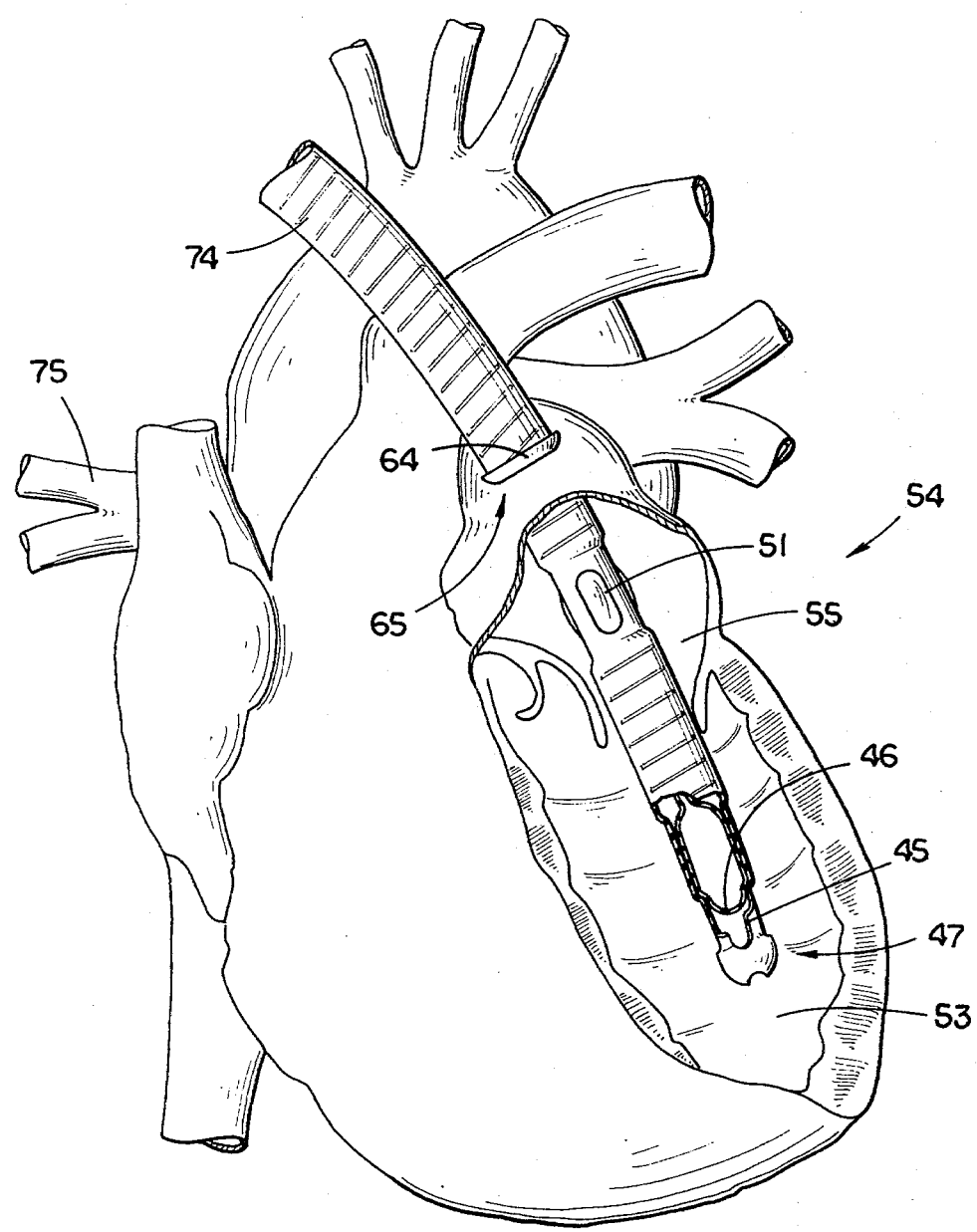
FIG. 10 is a representation of the cannula in FIG. 8 in use during a cardiac cannulation, with the first holes positioned in the left ventricle of the heart and the second more proximal holes positioned to drain blood from the left atrium area.

The modification in cannula 44 is the addition of a second plurality of holes 51 spaced apart proximally and axially along first member 52 from the first holes 45 adjacent its distal end 47. The purpose of the second set of holes is to permit the simultaneous drainage of blood from two separate areas during a cardiac cannulation procedure. For example, FIG. 10 depicts a simplified representation of an exposed heart 54 during cardiac cannulation using a cannula 74 similar to cannula 44 in FIG. 8. Distal end 47 has been surgically positioned in the left ventricle area 53 of the heart 54 for drainage purposes. Second holes 51, also by way of the surgical incision, are positioned in the left atrium area 55. Blood can therefore be simultaneously drained from both the left atrium and left ventricle areas during cannulation with the use of but a single cannula, or catheter, 74. A second example of the use of cannula 44 is by positioning the distal end and first holes in the inferior vena cava adjacent the heart with the second more proximal holes surgically located to simultaneously drain blood from the right atrium area during cannulation. Cannulas such as that in FIG. 8 may also have application in the future simultaneously reintroducing blood back into the circulating system through two separate infusion sites.

Referring back to FIG. 8, a second inflatable balloon 56 has been positioned within the lumen of first member 52 adjacent second holes 51. Second balloon 56, when inflated, completely occludes the lumen of first member 52 while also blocking, or occluding, second holes 51. In this way, the inflated second balloon 56 prevents the loss or entrance of any fluid, such as air or solution, through second holes 51 while also preventing the entrapment of any air in these second holes that could be subsequently released in the circulatory system.

The inflation and deflation of first and second balloons 46 and 56 in cannula 44 is accomplished by a single flexible tubular member 57 connecting the balloons in series for their simultaneous inflating and deflating by means of a single remote female adapter and syringe (both not shown), as previously discussed in connection with the preferred cannula 10. Tube 57 threads through a flexible tubular passageway or member 58 and a sealed adapter 61 to connect with this remote fluid supply to inflate and deflate the two balloons. Proper positioning of the balloons within the cannula lumen is again accomplished by means of a marker 62 properly positioned on tube 57 outside the sealed adapter. Also similar to preferred cannula 10, when ready to begin cannulating the heart, both balloons 46 and 56 are completely removed from the cannula lumen into the side passageway 58 by manually withdrawing tube 57 in the direction of arrow 59.

Although not incorporated into cannula 44, two further modifications are contemplated by applicant which may provide assistance in certain cannulation techniques. First, it is seen that independent inflating and deflating means such as tube 57 can be provided for the two intralumenal balloons. This independent control would permit drainage of blood from the more proximal second holes while maintaining the first balloon in its inflated occluding condition. Second, it is further contemplated that cannula apparatus incorporating applicant's invention can be constructed with two separate lumens within a single flexible tubular member, as by dividing the single lumen with a flexible film or wall. By then providing two independent balloons and two sets of holes similar to cannula 44, it is possible to occlude the proximal holes while deflating and retracting the more distal balloon from its separate lumen. In this way, and analogizing to FIG. 10, blood can be drained from the left ventricle area while no blood is drained from the left atrium area during a cardiac cannulation. Modifications such as these are clearly within the contemplation and scope of the disclosure herein and the claims attached hereto.

Referring again to FIG. 8, the distance 63 separating the first and second holes 45 and 51 can vary substantially according to design and other considerations. This distance is entirely dependent upon the two areas selected for drainage and the distance through the prepared incision separating these areas. Other factors such as the age of the person and the relative size of the heart must, of course, be taken into consideration in arriving at this required distance. Generally, distance 63 will vary between about 5 cm. and about 15 cm.

Cannula 44 includes two further improvements of importance to cardiac cannulation procedures. First, cannula 44 includes an enlarged circular marker 64 attached to the outer surface of first member 52 proximal of the second holes 51. This marker is precisely positioned along the tubular first member of the cannula and is useful to the surgeon as indicating the position of the cannulating holes during the insertion procedure.

Using FIG. 10 as an example, the surgeon has first determined the distance 63 required to properly position the first and second holes 45 and 51 in the left ventricle and left atrium areas 53 and 55, respectively. He has determined the point of initial entry into the circulatory system, generally indicated by arrow 65, and knows the distance the cannula must be inserted through the prepared incision for proper positioning. By attaching marker 64 at this required distance, e.g., as by sliding the marker along the outer surface of first member 52 or by some other commonly practiced technique, the surgeon inserts the cannula through the prepared incision until he feels, or sees, that the marker has reached its proper position as depicted in FIG. 10. The surgeon is then assured the cannulating holes are properly positioned can proceed to the next step in the procedure.

It should be noted that FIG. 10 depicts a pulmonary cannulation wherein entry was achieved through an incision in the upper left atrium area of the heart. Another accepted surgical procedure for cannulating these left atrium and left ventricle regions calls for entry through an incision in a pulmonary vein 75 which drains into a remote region in the left atrium not shown in FIG. 10.

The second additional feature incorporated into cannula 44 is a means including still another flexible tube or passageway 66 for infusing a solution into the cannulated heart of a person upon insertion and proper positioning of the cannula apparatus. In cannula 44, this means is accomplished by incorporating a passageway 66 into the wall of first member 52. This passageway includes an inlet end equipped with an appropriate female adapter or attachment 67 and at least one outlet or discharge opening 68 adjacent both the first and second holes 45 and 51.

This infusion tube, as it is commonly called, permits the ready infusion of blood or other solutions for a variety of purposes. For example, it is often desirable to infuse blood or some cooling crystalloid solution into the left ventricle or other area in the heart to provide additional cooling for myocardial protection. Multiple discharge openings 68 located circumferentially around the cannula are often desirable because they permit the cooling fluid to be injected evenly throughout the cannulated area thereby cooling the myocardial wall in preparation for further surgical procedures. The cooling fluid is siphoned out of the infused area by the heart-lung machine means via the multiple holes 45 and 51 positioned in the cannulated areas.

The method of using cannula 44 is as follows: First, lumen 72 of the cannula is filled with blood or a compatible electrolytic solution, first and second balloons 46 and 56 are properly positioned by manually threading tube 57 through the sealed adapter and tube 58, and the two balloons are inflated. Both the inflated balloons completely occlude the cannula lumen at their locations while balloon 46 only partially obstructs the first holes 45 whereas the second balloon completely blocks the more proximal holes 51. The order of these filling, positioning and inflating steps is not important. The only concern is to prevent the entrapment of any air within the cannula lumen. In the preferred method, cannula 44 is submerged in a tub of sterile saline solution where the positioning and inflating steps are then successfully performed.

With the cannula filled and occluded, distal end 47 is inserted through the prepared incision and the cannula is properly positioned within the circulatory system of the person with the aid of the previously metered and positioned marker 64. FIG. 10 depicts an example of a properly positioned cannula.

Drainage of both cardiac regions is then begun by deflating and retracting the balloons within the side passageway 58 and then starting the heart-lung machine means (not shown). When the operation is completed, the cannula is removed after first either clamping it or repositioning and reinflating the intralumenal balloons.

FIGS. 4 and 11 depict two cannula apparata 29 and 77 incorporating a further modification of the preferred cannula 10 and cannula 44 described above. Specifically, balloons 25 and 78 are positioned to occlude the entire intralumenal space in the distal end of the cannulas thus obstructing all distally positioned holes 16 and 82, including hole 83 located in the distal tip of cannula 77. This feature of totally obstructing the distal holes is beneficial when concern over vessel or cavity obstruction is minimal in relation to the concern over avoiding the introduction of entrapped air into the circulatory system.

For example, this modification is useful in draining a relatively large cavity such as the left ventricle depicted in FIG. 10 which has no major vessels either draining into or exiting the cavity to warrant much concern about possible obstruction problems. In this situation, there is little need for free flow, or wash, of blood across and through the unobstructed portion of the distal end of the cannula in contrast to the circumstance depicted in FIG. 6. The concern to avoid introducing entrapped air into the intracardial chamber is of first priority, and a cannula constructed and shown in FIGS. 4 and 11 is useful in guarding against this introduction.

As shown by the above disclosure, the method and cannula embodiments of the present invention permit cannulation of the heart and vessels without the risk of introducing trapped air into the circulatory system, as is common with prior art methods and apparata. The present embodiments eliminate the need for such external cannula manipulation as the venting of trapped air or the use of clamps to block secondary tubing while the cannula fills and often overflows with liquid.

It should also be noted that although the above embodiments have disclosed first and second pluralities of holes in the first tubular members, it is possible and even desirable under certain circumstances to employ only one hole in the cannula body. For example, one hole is ample to achieve proper infusion of blood back into the circulatory system through properly positioned arterial cannulas leading from the heart-lung machine means. Therefore, the use of only one hole in place of either the first or second pluralities, or both, is clearly within the scope and contemplation of the present invention as disclosed and claimed herein.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

I claim:

1. An extracorporeal cannula apparatus suitable for use in a cardiac cannulation, comprising:
   (a) a first elongated and flexible tubular member having a proximal and a distal end, the proximal end being open, said first member including at least one first hole near the distal end thereof;
   (b) a first inflatable balloon;
   (c) means for positioning said first balloon in the lumen of said first member adjacent the first hole therein and for occluding the lumen and for preventing the entrapment of air near the distal end thereof when said first balloon is inflated; and
   (d) means, including a flexible tubular member, for readily inflating and deflating said first balloon.

2. The apparatus of claim 1 wherein said means for positioning is also for allowing liquid to wash freely across and through the unobstructed portion of the distal end of said first member when said first balloon is inflated.

3. The apparatus of claim 1 or 2 wherein said means for positioning additionally includes means for retracting said first balloon from the lumen of said first member after its proper insertion during cardiac cannulation to prevent any possible interference with blood flow through said first member.

4. The apparatus of claim 3 wherein said means for positioning and for retracting and said means for inflating and deflating include:
   (a) a second flexible tubular member communicating with the lumen of said first member removed from the distal end thereof;
   (b) a third flexible tubular member extending from within said second member and communicating with said first balloon, said first balloon being retractable within said second member by manipulating said third member therein.

5. The apparatus of claim 3 additionally comprising means, including a flexible tubular passageway in said first member having an inlet opening near the proximal end thereof and an outlet opening near the distal end thereof, for infusing a solution upon insertion of the distal end of said first member into the circulatory system of a person during cannulation.

6. The apparatus of claim 3 wherein said first member includes a first plurality of holes near the distal end thereof.

7. The apparatus of claim 6 wherein said means for preventing is that said first balloon, when inflated, completely occludes the first holes and occupies the entire intraluminal space in the distal end of said first member to the exclusion of any entrapped air.

8. The apparatus of claim 6 wherein said means for positioning and for allowing is that the most distal portion of said first balloon, when inflated, extends to a point between the most distal portion and the most proximal portion of the first holes.

9. The apparatus of claim 3 wherein said first member further includes at least one second hole therein spaced apart axially from the first hole, the apparatus additionally comprising:
   (a) a second inflatable balloon;
   (b) means for positioning said second balloon in the lumen of said first member adjacent the second hole therein and for occluding the second hole and lumen and for preventing the entrapment of air near the distal end thereof when said second balloon is inflated; and
   (c) means, including a flexible tubular member, for readily inflating and deflating said second balloon.

10. The apparatus of claim 9 wherein said means for positioning and for retracting and said means for inflating and deflating said first and said second balloons include:
    (a) a second flexible tubular member communicating with the lumen of said first member removed from the distal end thereof;
    (b) a third flexible tubular member extending from within said second member and communicating with said first balloon, said first balloon being retractable within said second member by manipulating said third member therein.

11. The apparatus of claim 10 wherein said first member includes a second plurality of holes therein spaced apart axially from the first holes.

12. The apparatus of claim 11 wherein the first and the second holes are spaced apart along said first member a distance of between about 5 cm. and about 15 cm.

13. The apparatus of claim 11 wherein the distance separating the first and the second holes is sufficient to allow positioning of the distal end of said first member and the first holes therein in the inferior vena cava of a human heart while the second holes are positioned in the right atrium of the heart during cardiac cannulation.

14. The apparatus of claim 11 wherein the distance separating the first and the second holes is sufficient to allow positioning of the distal end of said first member and the first holes therein in the left ventricle of a human heart while the second holes are positioned in the left atrium of the heart during cardiac cannulation.

15. The apparatus of claim 11 additionally comprising means, including a flexible tubular passageway in said first member having an inlet opening near the proximal end thereof and an outlet opening near the first and the second holes therein for infusing a solution into the circulatory system of a person during cannulation.

16. The combination comprising:
    (a) a heart-lung machine means; and
    (b) the cannula apparatus of claim 15 connected to said machine means.

17. The apparatus of claim 1 or 2 wherein said first member includes a hole in the distal tip thereof.

18. The combination comprising:
   (a) a heart-lung machine means; and
   (b) the cannula-apparatus of claim 1 connected to said machine means.

19. A method for inserting a cannula during a cardiac cannulation technique, comprising the steps of:
   (a) filling the lumen of a cannula with liquid, the cannula including a first elongated flexible tubular member having a proximal and a distal end, the proximal end being open, the first member including at least one first hole near the distal end thereof;
   (b) positioning a first inflatable balloon in the lumen of the first member adjacent the first hole therein;
   (c) inflating the first balloon once positioned to occlude the lumen and prevent the entrapment of air near the distal end thereof;
   (d) inserting the filled and occluded cannula into the circulatory system of a person through a prepared incision;
   (e) deflating the first balloon to unocclude the cannula lumen and allow blood to flow therethrough; and
   (f) removing the deflated balloon from the cannula lumen to avoid any possible interference with the free flow of blood therethrough.

20. The method of claim 19 in which said positioning includes threading a second flexible tubular member with the first balloon attached thereto through a side-mounted passageway and the lumen of the first member until the first balloon reaches the first hole therein.

21. The method of claim 20 wherein said removing includes threading the second tubular member and the first balloon back through the cannula lumen and into the side passageway.

22. The method of claim 21 wherein said inflating and said deflating are by means of the second tubular member.

23. The method of claim 19 wherein said positioning and said inflating further comprise allowing liquid to wash freely across and through the unobstructed portion of the distal end of the first member upon insertion thereof into the circulatory system of a person.

24. The method of claim 23 additionally comprising infusing a solution into the cannulated areas in the circulatory system of the person during the cannulation procedure.

* * * * *